(12) United States Patent
Courtney et al.

(10) Patent No.: US 12,338,432 B2
(45) Date of Patent: Jun. 24, 2025

(54) SPERM CELL ISOLATION AND SPERM-ASSOCIATED DNA PURIFICATION

(71) Applicant: Promega Corporation, Madison, WI (US)

(72) Inventors: Nicholas Alan Courtney, Madison, WI (US); Margaret Mary Ewing, Middleton, WI (US); Robert Stewart McLaren, Oregon, WI (US); David Harrison Warshauer, Verona, WI (US)

(73) Assignee: Promega Corporation, Madison, WI (US)

( * ) Notice: Subject to any disclaimer, the term of this patent is extended or adjusted under 35 U.S.C. 154(b) by 231 days.

(21) Appl. No.: 17/199,173

(22) Filed: Mar. 11, 2021

(65) Prior Publication Data

US 2021/0284989 A1 Sep. 16, 2021

Related U.S. Application Data

(60) Provisional application No. 62/989,377, filed on Mar. 13, 2020.

(51) Int. Cl.
*C12N 15/10* (2006.01)
*C12Q 1/6806* (2018.01)
*C12Q 1/6888* (2018.01)
*G16B 50/00* (2019.01)

(52) U.S. Cl.
CPC ......... *C12N 15/101* (2013.01); *C12Q 1/6806* (2013.01); *C12Q 1/6888* (2013.01); *G16B 50/00* (2019.02)

(58) Field of Classification Search
CPC .. C12N 15/101; C12Q 1/6806; C12Q 1/6888; C12Q 2521/537; C12Q 2527/125; G16B 50/00
See application file for complete search history.

(56) References Cited

U.S. PATENT DOCUMENTS

| 5,034,506 A | 7/1991 | Summerton et al. |
| 7,320,891 B2 * | 1/2008 | Tereba ............... C12N 15/1003 435/325 |

FOREIGN PATENT DOCUMENTS

| WO | WO 2007/000972 | 1/2007 | |
| WO | WO-2007000972 A1 * | 1/2007 | ............. C12N 15/62 |
| WO | WO 2010/071833 | 6/2010 | |
| WO | WO 2017/162518 | 9/2017 | |

(Continued)

OTHER PUBLICATIONS

Promega (DNA IQ System) (DNA IQ™ System (promega.com)) (Year: 2023).*

(Continued)

*Primary Examiner* — Anna Skibinsky
*Assistant Examiner* — Morgan Taylor Lindgren Baltzel
(74) *Attorney, Agent, or Firm* — Casimir Jones, S.C.; David W. Staple

(57) ABSTRACT

Provided herein are methods, reagents, and kits for the isolation of sperm cells from other cell types and the purification of sperm-associated DNA from a complex sample. In particular, methods, reagents, and kits are provided for the separation of intact sperm cells from epithelial cells via binding of sperm cells to a cellulose material, and the extraction of sperm-associated DNA therefrom.

14 Claims, 11 Drawing Sheets

(56) References Cited

FOREIGN PATENT DOCUMENTS

WO    WO-2017162518 A1 *  9/2017   ......... C12N 15/1003

OTHER PUBLICATIONS

Preparation of Genomic DNA from Mammalian Sperm, Alexandra Weyrich, First published: Apr. 1, 2012 https://doi.org/10.1002/0471142727.mb0213s98 (Year: 2012).*

English translation of WO 2007000972, 16 pages (Year: 2023).*

Jenny A. Lounsbury, "Enhanced recovery of spermatozoa and comprehensive lysis of epithelial cells from sexual assault samples having a low cell counts or aged up to one year" Forensic Science International: Genetics vol. 8, Issue 1, Jan. 2014, pp. 84-89 received Sep. 12, 2012 (Year: 2012).*

Das S, Saha S, Majumder GC, Dungdung SR. Purification and characterization of a sperm motility inhibiting factor from caprine epididymal plasma. PLoS One. Aug. 10, 2010;5(8):e12039. doi: 10.1371/journal.pone.0012039. PMID: 20706623; PMCID: PMC2919373. (Year: 2010).*

International Search Report and Written Opinion for PCT/US21/21970. Mailed Jun. 9, 2021. 11 pages.

Anslinger et al., Application of sperm-specific antibodies for the separation of sperm from cell mixtures. Forensic Science International: Genetics Supplement Series, 2008. 1: 394-395.

Braasch et al., Novel antisense and peptide nucleic acid strategies for controlling gene expression. Biochemistry. Apr. 9, 2002;41(14):4503-10.

Butler. Advanced Topics in Forensic DNA Typing: Methodology, Elsevier Inc. 2011. TOC only. 4 pages.

Garvin et al., DNA preparation from sexual assault cases by selective degradation of contaminating DNA from the victim. J Forensic Sci. Nov. 2009;54(6):1297-303.

Gill et al., Forensic application of DNA 'fingerprints'. Nature. Dec. 12-18, 1985;318(6046):577-9.

Lehninger. DNA: The structure of Chromosomes and Genes. Principles of Biochemistry. Worth Publishers. 1982. 793-800. 24 pages.

Vandewoestyne et al., Laser capture microdissection in forensic research: a review. Int J Legal Med. Nov. 2010;124(6):513-21.

Wahlestedt et al., Potent and nontoxic antisense oligonucleotides containing locked nucleic acids. Proc Natl Acad Sci U S A. May 9, 2000;97(10):5633-8.

Wang et al., Cyclohexene Nucleic Acids (CeNA): Serum Stable Oligonucleotides that Activate RNase H and Increase Duplex Stability with Complementary RNA. J. Am. Chem. Soc., 2000. 122: 8595-8602.

Yoshida et al., The modified method of two-step differential extraction of sperm and vaginal epithelial cell DNA from vaginal fluid mixed with semen. Forensic Sci Int. Mar. 21, 1995;72(1):25-33.

Zhao et al., Isolating Sperm from Cell Mixtures Using Magnetic Beads Coupled with an Anti-PH-20 Antibody for Forensic DNA Analysis. PLoS One. Jul. 21, 2016;11(7):e0159401. 9 pages.

* cited by examiner

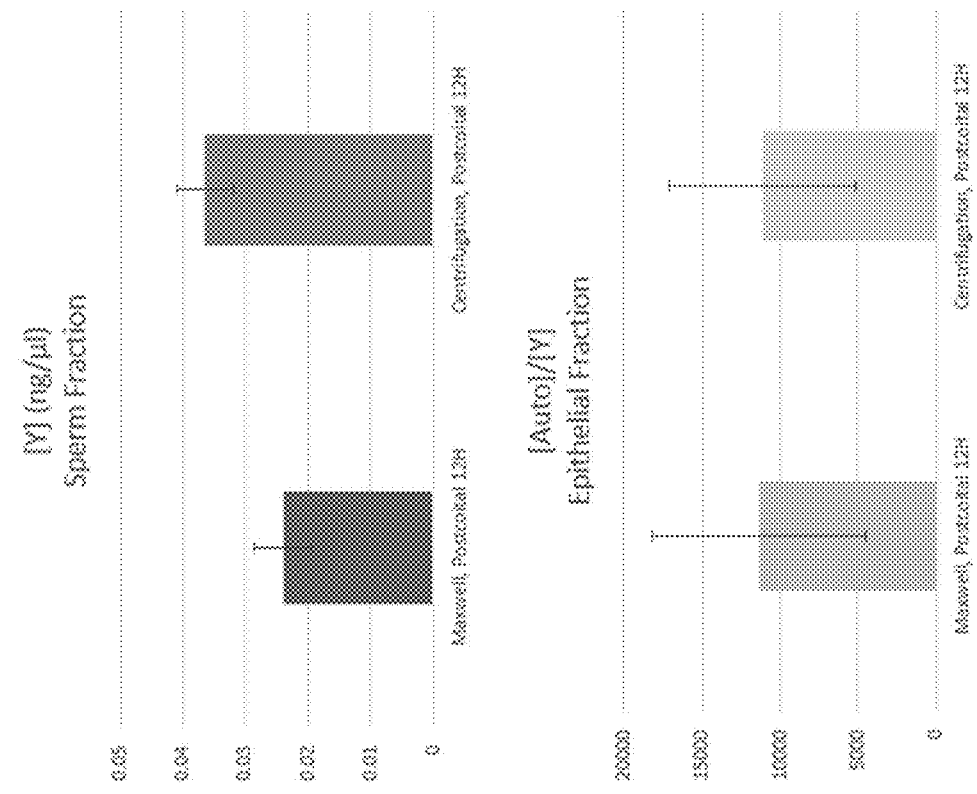
FIG. 7B
FIG. 7D
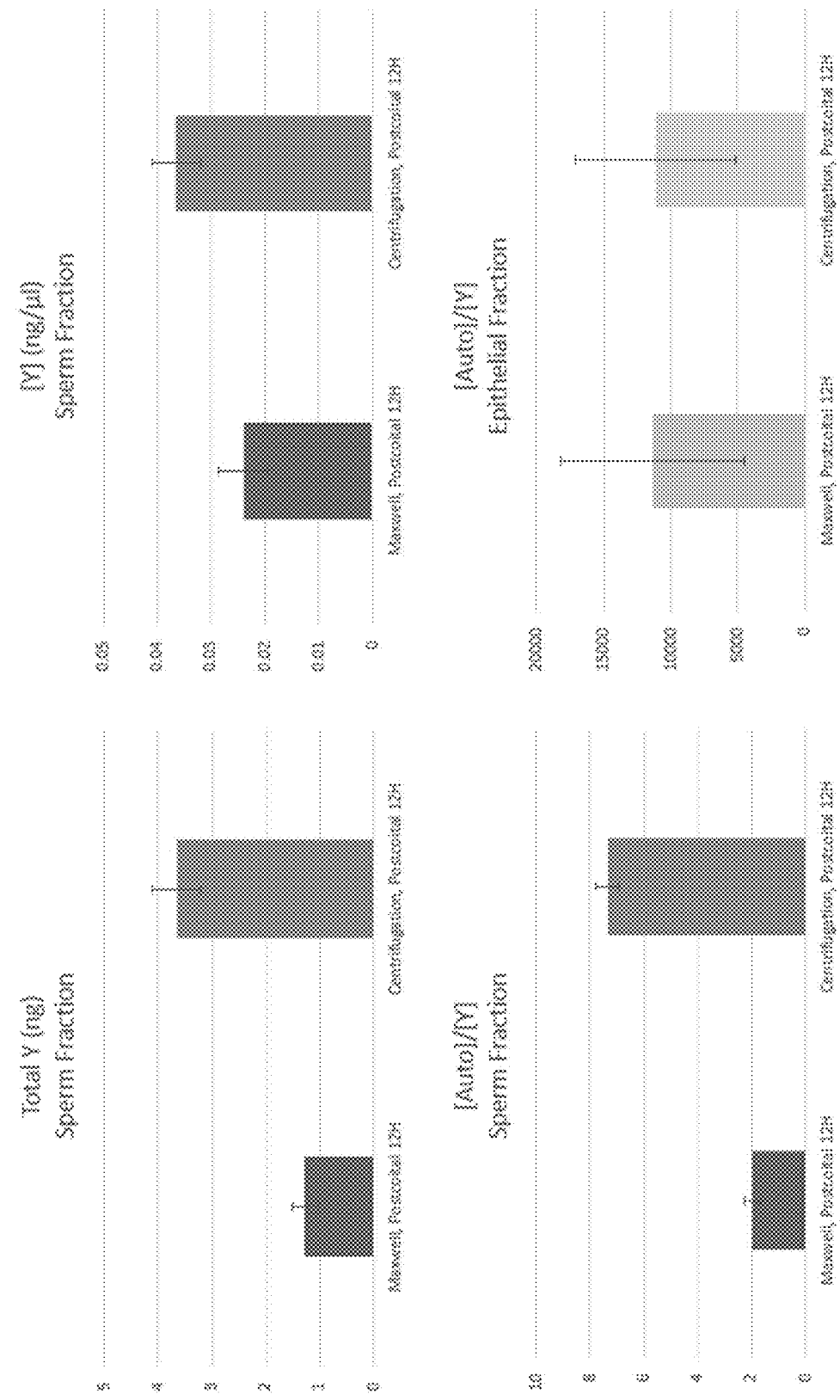
FIG. 7A
FIG. 7C

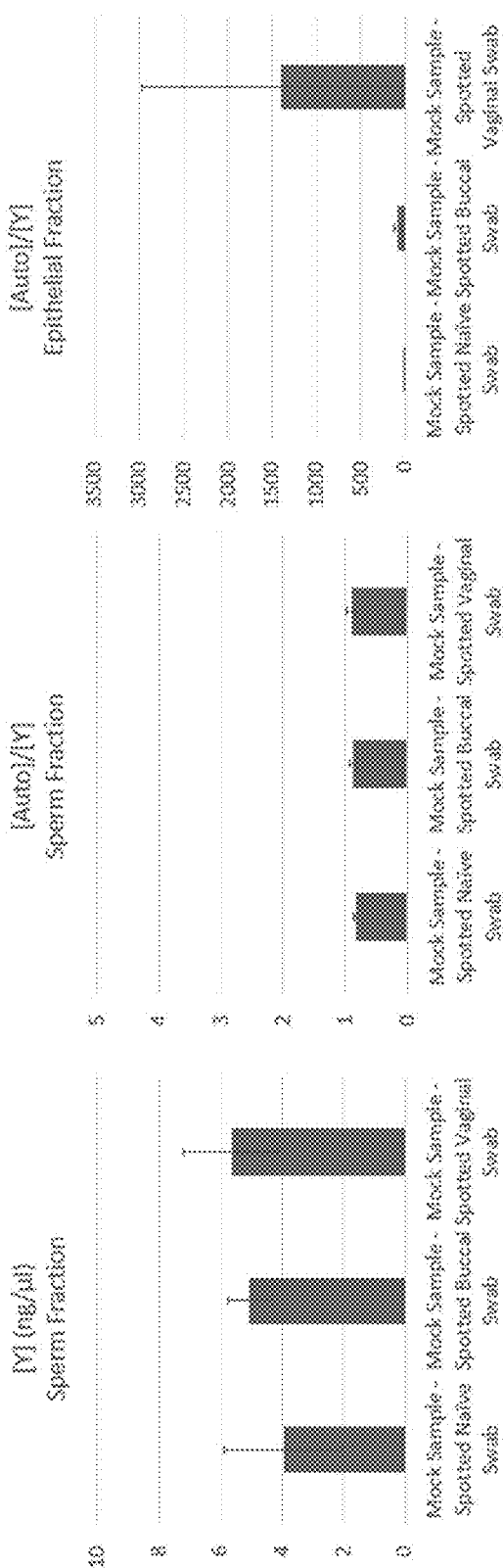

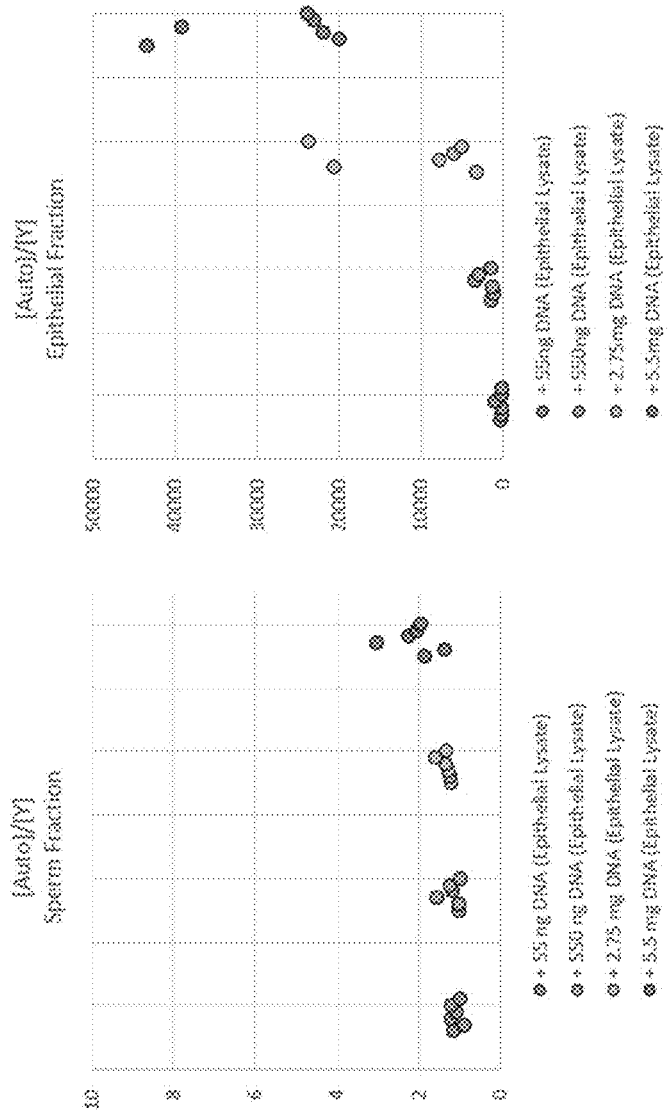
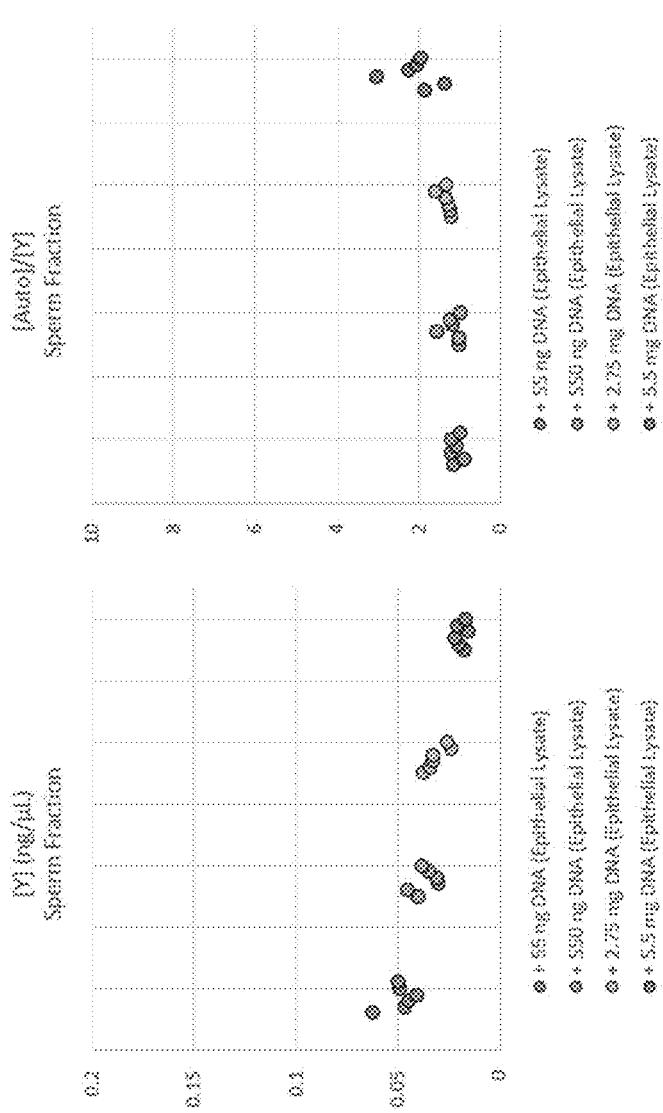
FIG. 11A  FIG. 11B  FIG. 11C

SPERM CELL ISOLATION AND SPERM-ASSOCIATED DNA PURIFICATION

CROSS-REFERENCE TO RELATED APPLICATION

The present application claims priority to U.S. Provisional Patent Application Ser. No. 62/989,377, filed Mar. 13, 2020, which is hereby incorporated by reference in its entirety.

FIELD

Provided herein are methods, reagents, and kits for the isolation of sperm cells from other cell types and the purification of sperm-associated DNA from a complex sample. In particular, methods, reagents, and kits are provided for the separation of intact sperm cells from epithelial cells via binding of sperm cells to a cellulose material, and the extraction of sperm-associated DNA therefrom.

BACKGROUND

In the field of forensic DNA analysis, there is a major need to be able to efficiently separate sperm-associated DNA from materials collected with a sexual assault kit, including the victim's DNA. Clean separation of sperm-associated DNA is essential to obtaining short tandem repeat (STR) profiles of potential suspects. The most common process for separating sperm-associated DNA, termed Differential Extraction (DE), is a labor-intensive protocol that requires a high degree of technical prowess and is incompatible with most automation techniques. In part due to the difficulties of the current protocol, there is a significant nationwide back log of sexual assault kits that are awaiting testing.

Thus, there remains a need for easy to use, cost-effective methods and kits for isolating sperm-associated DNA.

SUMMARY

Provided herein are methods, reagents, and kits for the isolation of sperm cells from other cell types and the purification of sperm-associated DNA from a complex sample. In particular, methods, reagents, and kits are provided for the separation of intact sperm cells from epithelial cells via binding of sperm cells to a cellulose material, and the extraction of sperm-associated DNA therefrom.

Specifically, the disclosure provides a method comprising: (a) contacting a sample comprising sperm cells with a digestion agent (or concentration of digestion agent) capable of efficiently lysing epithelial cells, but not sperm cells; (b) removing the digestion agent from the sperm cells, inactivating the digestion agent, or allowing the digestion agent to become inactivated; (c) adding a reducing agent to sperm cells, wherein the reducing agent breaks disulfide bonds present on the sperm cells; (d) contacting the sperm cells with a cellulose resin; (e) washing the cellulose resin with a wash buffer; and (f) eluting sperm-associated DNA from the cellulose resin.

The disclosure also provides a method comprising: (a) adding a reducing agent to a sample comprising sperm cells, wherein the reducing agent is sufficient in concentration to break disulfide bonds present on the sperm cells but not to lyse the sperm cells; (b) contacting the sample with a cellulose resin; (c) washing the cellulose resin with a wash buffer; and (d) eluting sperm-associated DNA from the cellulose resin.

The disclosure further provides a kit comprising two or more of: (a) a digestion agent capable of efficiently lysing epithelial cells but not sperm cells; (b) a reducing agent capable of breaking disulfide bonds present on sperm cells; (c) a cellulose resin; (d) a resuspension buffer; (e) a wash buffer; and (f) an elution buffer comprising a digestion agent and a reducing agent.

BRIEF DESCRIPTION OF THE DRAWINGS

FIGS. 7A-D is a set of graphs demonstrating that the methods described herein can purify sperm-associated DNA from post coital samples. For these data, postcoital swabs were collected from a consensual donor 12 hours post intercourse, and swabs were analyzed approximately one month after the collection date. Panels A and B show the overall yield of sperm-associated DNA (FIG. 7A) and the concentration of this DNA in the eluate (FIG. 7B). Panels C and D demonstrate the purity of sperm-associated DNA in the eluate (FIG. 7C), as indicated by the [Auto]/[Y] ratio, in comparison to the epithelial fraction (FIG. 7D). Data were obtained from a single experiment (n=4 for each condition) and quantified using the POWERQUANT® System (Promega Corp, Madison, WI); bars represent the mean±the standard deviation.

FIGS. 8A-C is a set of graphs showing that the methods described herein yield sperm-associate DNA when utilizing alternate parameters for the initial digestion. For this experiment, the initial digestion step was modified such that samples were incubated at 70° C. for 30 minutes; mock samples were prepared by spotting 1 μl of semen onto each of the indicated types of swabs. FIG. 8A shows the yield of sperm-associated DNA in the sperm fraction, FIG. 8B demonstrates the purity of the sperm fraction, and FIG. 8C quantifies the amount of non-sperm DNA in the epithelial fraction. Data were obtained from a single experiment (n=4 for each condition) and quantified using the POWERQUANT® System (Promega Corp, Madison, WI); bars represent the mean±the standard deviation.

FIG. 10A shows the yield of sperm-associated DNA from these samples; eluates are ~50 μl in volume. FIG. 10B depicts the same data as FIG. 10A; however, the axes have been modified to better illustrate samples with lower sperm counts. This experiment utilized the alternate digestion protocol of 70° C. for 30 minutes. Data were obtained from a single experiment (n=6 for each condition) and quantified using the POWERQUANT® System (Promega Corp, Madison, WI); bars represent the mean±the standard deviation while dots represent an individual sample.

FIGS. 11A-C is a set of graphs demonstrating the specificity of the methods described herein. For this experiment, samples were created by mixing a fixed amount of semen (0.005 μl) with the indicated amount of epithelial cell lysate; epithelial cell lysate was derived from pooled buccal swabs digested with the Digestion Buffer described herein. The mixed samples were then subjected to the full method, including the pre-processing steps. FIG. 11A shows the yield of sperm-associated DNA in the sperm fraction. FIG. 11B shows the purity of the sperm fraction, as indicated by the [Auto]/[Y] ratio. FIG. 11C shows the [Auto]/[Y] ratio of the epithelial fraction. This experiment utilized the alternate digestion protocol of 70° C. for 30 minutes. Data were obtained from a single experiment (n=6 for each condition) and quantified using the POWERQUANT® System (Promega Corp, Madison, WI); each dot represents an individual sample.

DEFINITIONS

Figure 1:
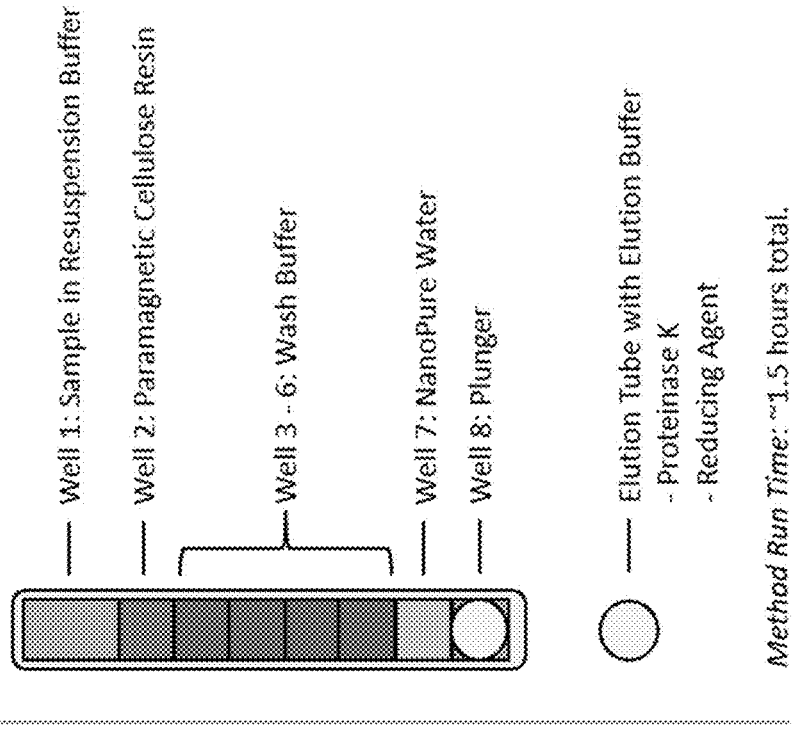
FIG. 1 is a schematic diagram illustrating an exemplary embodiment of the methods described herein.

To facilitate an understanding of the present technology, a number of terms and phrases are defined below. Additional definitions are set forth throughout the detailed description.

The terms "nucleic acid", "polynucleotide", "nucleotide sequence", and "oligonucleotide" are used interchangeably herein and refer to a polymer or oligomer of pyrimidine and/or purine bases, preferably cytosine, thymine, and uracil, and adenine and guanine, respectively (See Albert L. Lehninger, *Principles of Biochemistry*, at 793-800 (Worth Pub. 1982)). The terms encompass any deoxyribonucleotide, ribonucleotide, or peptide nucleic acid component, and any chemical variants thereof, such as methylated, hydroxymethylated, or glycosylated forms of these bases. The polymers or oligomers may be heterogenous or homogenous in composition, may be isolated from naturally occurring sources, or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. In some embodiments, a nucleic acid or nucleic acid sequence comprises other kinds of nucleic acid structures such as, for instance, a DNA/RNA helix, peptide nucleic acid (PNA), morpholino nucleic acid (see, e.g., Braasch and Corey, *Biochemistry*, 41(14): 4503-4510 (2002) and U.S. Pat. No. 5,034,506), locked nucleic acid (LNA; see Wahlestedt et al., *Proc. Natl. Acad. Sci. U.S.A.*, 97: 5633-5638 (2000)), cyclohexenyl nucleic acids (see Wang, *J. Am. Chem. Soc.*, 122: 8595-8602 (2000)), and/or a ribozyme. The terms "nucleic acid" and "nucleic acid sequence" may also encompass a chain comprising non-natural nucleotides, modified nucleotides, and/or non-nucleotide building blocks that can exhibit the same function as natural nucleotides (e.g., "nucleotide analogs").

As used herein, the term "sperm-associated DNA" refers to any DNA sequence that is present within, or otherwise attached to, a sperm cell.

The terms "peptide", "polypeptide", and "protein" are used interchangeably herein and refer to a polymeric form of amino acids comprising at least two or more contiguous amino acids, which can include coded and non-coded amino acids, chemically or biochemically modified or derivatized amino acids, and polypeptides having modified peptide backbones.

The term "differential extraction" refers to extraction methods utilized to extract a subset of cell types from a heterogeneous population of cells. In certain embodiments, differential extraction includes the selective lysis of non-sperm cells in a mixture of sperm cells and non-sperm cells, including, but not limited to, epithelial cells. Differential extraction also is referred to in the art as "differential isolation."

The term "biological sample", as used herein, refers to any sample that contains at least one biological material. Exemplary biological materials include, but are not limited to, blood, saliva, skin, feces, urine, sperm cells, epithelial cells (including, but not limited to, vaginal epithelial cells), muscle tissue, and bone.

The term "forensic sample", as used herein, refers to a biological sample obtained to address identity issues arising in legal contexts, including, but not limited to murder, rape, trauma, assault, battery, theft, burglary, other criminal matters, identity, parental or paternity testing, and mixed DNA samples.

The term "epithelial cell", as used herein, refers to a cell that forms the tissues that line the outer surfaces of organs and blood vessels throughout an animal (e.g., a mammal) as well as the inner surfaces of cavities in many internal organs.

The term "sperm cell", as used herein, refers to the reproductive cell of a male animal, such as a male mammal (e.g., a human), which can unite with an egg cell of a female animal to form a zygote.

The terms "digestion agent" and "lysis agent" are used interchangeably herein to refer to a substance or compound that disrupts and breaks open (lyses) cells. A digestion agent or lysis agent may be present in a buffer, which typically is referred to in the art as a "lysis buffer". Examples of digestion or lysis agents include, but are not limited to, detergents (Tween-20, Triton X-100), surfactants (e.g., sodium dodecyl sulfate (SDS) or sodium lauryl sulfate (SLS)), and proteases (e.g., proteinase K). Certain exemplary lysis buffers are known in the art, and one skilled in the art can select a lysis buffer based on the intended use. In some embodiments, a concentration of a particular digestion agent exists in which the digestion agent is capable of disrupting and breaking open non-sperm cells (e.g., epithelial cells), but not sperm cells; at a higher concentration, the digestion agent will also disrupt and breaks open sperm cells.

The term "lysate" refers to a liquid phase containing lysed cell debris and DNA. A "whole cell lysate" contains all the contents of a lysed cell. A "processed cell lysate" has been processed (e.g., centrifuged, filtered, etc.) to remove a portion of the contents from the cell lysate. Certain embodiments herein utilize whole or processed cell lysates. Embodiments herein referring to "cell lysates" may find use with whole or processed cell lysates, unless otherwise indicated.

The term "reducing agent", as used herein, refers to an agent that reduces disulfide bonds, e.g., in proteins, by donating an electron to another chemical species in a redox chemical reaction. In certain embodiments, a reducing agent disrupts protamine disulfide bridges in sperm cells and disulfide bonds that maintain the structure of the sperm head. Disulfide bond reducing agents can be water-insoluble or water soluble. Exemplary reducing agents include, but are not limited to, dithiothreitol (DTT), Tris(2-carboxyethyl) phosphine hydrochloride (TCEP), glutathione (GSH), 1-thioglycerol, and mercaptoethanol (ME).

The term "cartridge" refers to a system that comprises a plurality of compartments and does not contain sufficient fluid and/or magnetic particle handling mechanisms to function independently of a separate fluid-handling and/or magnetic particle-handling instrument. A cartridge may be, in certain embodiments, designed for a single use, after which it is discarded. In certain embodiments, one or more of the compartments in a cartridge contains a reagent. In other embodiments, all of the compartments of a cartridge are contained in a single unit. In certain embodiments, the compartments of a cartridge are divided between two or more units that together form the cartridge. A single cartridge may be designed to process 1, 2, 4, 6, 8, 12, 16, 24, 48, 96, or more than 96 samples. In various embodiments, a cartridge is designed to process between 1 and 48 samples, between 1 and 24 samples, between 2 and 24 samples, between 1 and 16 samples, or between 2 and 16 samples. When a cartridge is designed to process at least two samples, it may be designed to process at least two of the samples simultaneously. In certain embodiments, a cartridge is designed to process all of the samples simultaneously.

DETAILED DESCRIPTION

Provided herein are methods, reagents, and kits for the isolation of sperm cells from other cell types and the purification of sperm-associated DNA from a complex sample. In particular, methods, reagents, and kits are provided for the separation of intact sperm cells from epithelial cells via binding of sperm cells to a cellulose material, and the extraction of sperm-associated DNA therefrom.

Experiments conducted during development of embodiments described herein demonstrate a direct binding interaction between sperm cells and cellulose material (e.g., cellulose resin). Methods, reagents, and kits described herein utilize this interaction for the separation of sperm cells from sample contaminants and epithelial cells, and for the purification of sperm-associated DNA from the sample. In some embodiments, provided herein are processes for binding sperm cells, and their associated DNA, to a paramagnetic cellulose resin; this binding interaction provides for streamlined and automated methods for handling the sperm cells, isolating sperm-associated DNA, and for separating them from other contaminating substances, such as epithelial cells and contaminating DNA.

Methods described herein, and kits, reagents, and devices for performing such methods, differ from some existing methods in that sperm cells are separated intact from a sample (e.g., containing non-sperm cells (e.g., epithelial cells), containing other contaminants (e.g., a sample collection device (e.g., swab tip), buffer, biological fluid components, environmental debris, etc.), and sperm-associated DNA is subsequently extracted/purified from the isolated sperm cells. In common differential extraction techniques, use is made of the differential lysis of non-sperm (e.g., epithelial cells) and sperm cells to isolate DNA from each cell type. These methods rely on the laborious physical separation (e.g., repeated centrifugation steps) of sperm cells from non-sperm cell lysates to allow isolation of sperm-associated DNA that is free of non-sperm (e.g., epithelial cells) DNA contamination. The methods and reagents provided herein allow for simplification of this process by binding sperm cells to paramagnetic particles allowing automation of the process of sperm cell enrichment and sperm-associated DNA purification.

The disclosure provides a method comprising (a) contacting a sample comprising sperm cells with a digestion agent (or concentration of a digestion agent) capable of efficiently lysing epithelial cells, but not sperm cells; (b) removing the digestion agent from the sperm cells, inactivating the digestion agent, or allowing the digestion agent to become inactivated; (c) adding a reducing agent to sperm cells, wherein the reducing agent breaks disulfide bonds present on the sperm cells; (d) contacting the sperm cells with a cellulose resin; (e) washing the cellulose resin with a wash buffer; and (f) eluting sperm-associated DNA from the cellulose resin. The sample may be any suitable biological sample described herein. In some embodiments, the sample is a forensic sample which may comprise a mixture of different cell types, depending on the source of the sample. For example, the sample may comprise a mixture of epithelial cells and sperm cells.

A sample comprising sperm cells may be contacted (e.g., mixed) with any suitable digestion agent that is capable of efficiently lysing epithelial cells but not sperm cells. In some embodiments, a sample is contacted with a suitable concentration of a digestion agent that is capable of efficiently lysing epithelial cells but not sperm cells. In some embodiments, at a higher concentration, the same digestion agent is also capable of lysing sperm cells. It will be appreciated that sperm cells are protected from conventional digestion agents and lysis buffers due to the high abundance of disulfide bonds on sperm cells. Any suitable digestion agent known in the art and described herein may be used. In some embodiments, the digestion agent comprises a protease, such as proteinase K. In other embodiments, the digestion agent comprises a surfactant. Ideally, the digestion agent comprises both a protease and a surfactant. For example, the digestion agent may comprise proteinase K and sodium dodecyl sulfate (SDS). Whatever digestion agent is employed, the digestion agent desirably lyses at least 95% (e.g., 96%, 97%, 98%, 99%, or 100%) of the epithelial cells present in the sample. Along the same line, the digestion agent desirably lyses less than 25% (e.g., 20%, 15%, 10%, 5%, or 0%) of sperm cells present in the sample. In some embodiments, the digestion agent comprises a starting or final concentration of 0.01% to 1.0% (e.g., 0.01%, 0.02%, 0.05%, 0.1%, 0.2%, 0.5%, 1.0%, or ranges therebetween) surfactant (e.g., SDS). In some embodiments, the digestion agent comprises a starting or final concentration of 1 µg/ml to 100 µg/ml (e.g., 1 µg/ml, 2 µg/ml, 5 µg/ml, 10 µg/ml, 50 µg/ml, 100 µg/ml, or ranges therebetween) protease (e.g., proteinase K).

In some embodiments, once sufficient digestion of epithelial cells (but not sperm cells) present in the sample has occurred, removal or inactivation of the digestion agent provides for optimal recovery of sperm-associated DNA. In this regard, the digestion agent may be removed from the sperm cells or inactivated, either actively or passively (e.g., by allowing the digestion agent to become inactivated). When the digestion agent comprises proteinase K, inactivation desirably comprises providing sufficient time to allow the proteinase K to self-inactivate (i.e., auto-proteolyze). Ideally, autoproteolysis of proteinase K is allowed to proceed to at least 95% (e.g., 96%, 97%, 98%, 99%, or 100%) inactivation of the proteinase K. In some embodiments, autoproteolytic digestion of the proteinase K is accelerated by depletion of calcium in the reaction mixture. Other methods for inactivating digestive agents include, for example, heat treatment (e.g., incubation above 70° C.), a change in pH, or the use of a chemical inhibitor.

In certain embodiments, the digested sample may be centrifuged to remove any solid substrate present in the initial sample (e.g., a swab) and pellet the intact sperm cells. The resulting supernatant may be retained as a sperm-cell-depleted fraction. In other words, the method may comprise separating a sperm-cell-enriched fraction (i.e., centrifuged pellet) of the sample from a sperm-cell-depleted fraction (i.e., supernatant) of the sample. It will be appreciated that the sperm-cell-depleted fraction contains epithelial cells present in the sample (e.g., lysed epithelial cells), and the sperm-cell-depleted fraction may be retained for subsequent analysis or discarded.

In some embodiments, sperm-depleted DNA may be obtained from the sperm-cell-depleted fraction and analyzed. For example, sperm-depleted DNA may be quantified or genotyped. Methods for quantifying DNA are known in the art and include, for example, spectrophotometry, fluorescence, real-time PCR (also known as quantitative PCR (qPCR)), and digital PCR technologies. Genotyping the sperm-depleted DNA may be performed using any suitable method known in the art. Such methods include, for example, short tandem repeat (STR) analysis, restriction fragment length polymorphism (RFLP) of genomic DNA, random amplified polymorphic detection (RAPD) of genomic DNA, amplified fragment length polymorphism (AFLP) detection, single nucleotide polymorphism (SNP) detection, polymerase chain reaction (PCR), DNA sequencing, allele specific oligonucleotide (ASO) probes, and hybridization to DNA microarrays or beads.

In certain embodiments, the sperm-depleted DNA is genotyped using short tandem repeat (STR) analysis. STRs are repetitive sequence elements 3-7 base pairs (bp) in length scattered throughout the human genome. By amplifying and analyzing these polymorphic loci, and then comparing the resulting STR profile to that of a reference sample, the origin of biological samples such as cells or tissues can be identified and verified. STR analysis is used in forensic science to evaluate specific STR regions found on nuclear DNA. In various embodiments, loci containing 3 bp (trinucleotide), 4 bp (tetranucleotide), and/or 5 bp repeat sequences are used for human identification. Four and 5 bp repeat sequences are found throughout the human genome and are, in certain instances, highly polymorphic. The number of alleles at a tetranucleotide repeat STR locus ranges, in various embodiments, from about 4 to about 20.

In certain embodiments, when isolated DNA is used for detection of polymorphic STRs, the amplified alleles from the individual DNA samples can be compared to one or more size standards, e.g., commercial DNA markers and/or locus-specific allelic ladders, to determine the alleles present at each locus. In certain embodiments, allelic ladders comprise two or more distinct lengths of DNA representing two or more known alleles from a particular locus. DNA may be visualized by any suitable technique known in the art, including, but not limited to, silver staining, radioactive labeling, fluorescent labeling, and using various dyes and stains. In certain embodiments, prior to visualization, DNA is separated using denaturing or native gel electrophoresis, or any other size separation method. In certain embodiments, amplified alleles are subjected to DNA sequence analysis. Exemplary methods for DNA amplification, genotyping, and analysis are known in the art and are described, e.g., Butler, John M., *Advanced Topics in Forensic DNA Typing: Methodology*, Elsevier Inc.: MA, USA (2011).

Following complete inactivation of the digesting agent, a reducing agent is added to sperm cells, wherein the reducing agent breaks disulfide bonds present on the sperm cells. Exemplary reducing agents that can be employed in the disclosed method are known in the art. Such reducing agents include, but are not limited to, dithiothreitol (DTT), tris(2-carboxyethyl) phosphine (TCEP), 2-mercaptoethanol (BME), and/or 1-thioglycerol (1-TG). In certain embodiments, the reducing agent comprises 1-thioglycerol (1-TG). Any suitable amount of reducing agent may be added to the sperm cells as long as the concentration of reducing agent is sufficient to break disulfide bonds present on the sperm cells without lysing the sperm cells. When the reducing agent is 1-TG, the concentration of 1-TG added to the sperm cells is between about 10 mM and about 25 mM (e.g., 11 mM, 12 mM, 13 mM, 14 mM, 15 mM, 16 mM, 17 mM, 18 mM, 19 mM, 20 mM, 21 mM, 22 mM, 23 mM, or 24 mM). In one embodiment, the concentration of 1-TG added to the sperm cells is between about 11.5 and 23 mM. When other reducing agents are used, concentrations sufficient to yield similar reduction of disulfide bonds as the 1-TG concentrations above and used herein may be employed. Importantly, omission or insufficient amounts of reducing agent have been shown to impair binding of sperm cells to the cellulose resin. For example, omission of 1-TG reduces the overall sperm-associated DNA yield by approximately 90%. The disclosure also provides a method comprising: (a) adding a reducing agent to a sample comprising sperm cells, wherein the reducing agent is sufficient in concentration to break disulfide bonds present on the sperm cells but not to lyse the sperm cells; (b) contacting the sample comprising sperm cells with a cellulose resin; (c) washing the cellulose resin with a wash buffer; and (d) eluting sperm-associated DNA from the cellulose resin.

In some embodiments, prolonged incubation of sperm cells with reducing agent (e.g., >30 minutes) at ambient temperature prior to exposure to cellulose resin may reduce overall sperm-associated DNA yield. The sample comprising reduced sperm cells may be contacted with any suitable cellulose resin, and sperm cells can be isolated from the sample by virtue of their ability to bind cellulose resin with high affinity. A variety of cellulose-based resins and matrices that may be used in the disclosed methods and kits are known in the art and are commercially available. In some embodiments, the cellulose resin comprises cellulose particles that contain an iron core or an iron oxide core. In certain embodiments, the cellulose resin comprises a paramagnetic cellulose resin. The term "paramagnetic," as used herein, refers to a body or substance that, when placed in a magnetic field, possesses magnetization in direct proportion to the field strength.

A paramagnetic cellulose resin as described herein may be used with the MAXWELL® RSC 48 Instrument and MAXWELL® 16 Instrument (Promega, Madison, WI). The MAXWELL® RSC 48 Instrument is a compact, automated nucleic acid purification platform that processes up to 48 samples simultaneously. MAXWELL® 16 instruments purify samples using paramagnetic particles (PMPs), which provide a mobile solid phase that optimizes capture, washing, and elution of the target material. MAXWELL® 16 instruments are magnetic particle handlers that efficiently preprocess liquid and solid samples, transport the PMPs through purification reagents in the prefilled cartridges, and mix during processing (see Technical Manuals for MAXWELL® 16 (TM295), MAXWELL® 16 Forensic (TM321), MAXWELL® FSC (TM462), and MAXWELL® RSC 48 (TM510)).

The cellulose resin and the sperm cell-containing sample desirably are incubated for a sufficient amount of time to ensure efficient binding of sperm cells to the resin. For example, the sperm cell-containing sample and the cellulose resin may be incubated together for at least about 5 minutes, about 10 minutes, about 15 minutes, about 20 minutes, about 30 minutes, about 45 minutes, about 50 minutes, about 1 hour, about 90 minutes, or about 2 hours. Following a suitable incubation time, the cellulose resin is washed with a wash buffer. The term "wash buffer," as used herein, refers to a buffer which removes contaminants from the cellulose resin, while allowing sperm cells to remain bound to the cellulose resin. Exemplary wash buffers include, but are not limited to, a detergent (e.g., SDS) and pH buffer (e.g., phosphate buffered saline (PBS) and Tris-HCl, pH 8). One of ordinary skill in the art can select a suitable wash buffer according to the sample type and reaction conditions.

In certain embodiments, the sperm-associated DNA may be eluted from the cellulose resin using an elution buffer. The term "elution buffer," as used herein, refers to a buffer that releases sperm-associated DNA, in particular by lysing the sperm cells bound to the sperm-binding particles. Certain exemplary elution buffers may comprise a digestion agent (as described herein) and/or a reducing agent (as described herein). In certain embodiments, the elution buffer comprises both a digestion agent and a reducing agent. For example, the digestion agent may comprise proteinase K and the reducing agent may comprise DTT, TCEP, BME, and/or 1-TG. One of ordinary skill in the art can select a suitable elution buffer according to the sample type and cellulose resin used. In certain embodiments, the sperm-associated DNA may be eluted from the cellulose resin by heating the cellulose resin in the elution buffer. For example, the cellulose resin may be heated by raising the temperature to at least 37° C.

The sperm-associated DNA eluted from the cellulose resin may then be analyzed. For example, the sperm-associated DNA may be quantified or genotyped, using similar methods as previously described herein with respect to analysis of a sperm cell-depleted fraction. In certain embodiments, the eluted sperm-associated DNA is genotyped using STR analysis.

The disclosure further provides a method of forensic analysis which comprises performing any of the method steps described herein, and comparing the sperm-associated DNA of the sample with a reference sample and/or a database. The term "forensic analysis" is used generally to refer to an investigation of a crime or security incident. The analysis of DNA samples obtained from a suspect or victim, often referred to in the art as "DNA profiling," is a major component of forensic analyses, depending on the nature of the crime or security incident. The term "reference sample", as used herein, refers to a sample of an individual's DNA (e.g., a crime suspect or victim) against which the sperm-associated DNA is compared. Reference samples are typically collected through a buccal swab. The reference sample is analyzed, e.g., by genotyping methods described herein, to create the individual's DNA profile. The DNA profile is then compared against the sperm-associated DNA isolated in accordance with the methods disclosed herein to determine whether there is a genetic match. In other words, the method comprises determining whether a particular subject is the source of the sperm cells in the sample. In some embodiments, the sperm-associated DNA may be compared against DNA sequences in a database or other repository. Exemplary databases include, but are not limited to, the Combined DNA Index System (CODIS), which is maintained by the U.S. Federal Bureau of Investigation (FBI), and the United Kingdom National DNA Database (NDNAD).

In certain embodiments, one or more of the method steps described herein may be automated. It will be appreciated that automated sample preparation provides significant benefits to laboratories, allowing users to focus on more detailed work while reducing the risk of exposure to chemicals and the need for repetitive motions, such as pipetting. In this regard, one or more of the steps described herein may be performed by an automated liquid handler.

Automated liquid handlers allow laboratories to handle increased sample processing demands while minimizing the need to increase headcount. Automated liquid handlers are commercially available from a variety of sources, including, but not limited to, the MAXPREP™ Liquid Handler combined with the MAXWELL® extraction available from Promega Corp. (Madison, WI).

In addition to or alternatively, one or more of the steps described herein may be performed by an automated particle handler, which moves particles (e.g., paramagnetic particles) instead of liquids. Automated particle handlers present minimal risk of cross-contamination because no liquid handling or splashing occurs during sample processing.

An exemplary embodiment of the methods described herein is depicted in FIG. 1. The method begins by digesting a sample and/or substrate (37° C., 10 minutes) in a buffer that contains both sodium dodecyl sulfate (SDS, 0.1%) and proteinase K (ProK, 2.5 µg/ml). Alternative digestion buffers are contemplated. The digestion step lyses epithelial cells while leaving sperm cells intact; sperm cells are protected from lysis due to their high abundance of disulfide bonds. In some embodiments, the digestion step is taken to completion, such that the ProK self-inactivates (auto-proteolyzes) before proceeding to the next step in the process. The use of active ProK in subsequent steps will interfere with sperm cell binding. Following the initial digestion, samples are centrifuged through a spin basket (16,000×g; 5 minutes). The centrifugation step (1) allows for the removal of a solid sample substrate (such as a swab) and (2) pellets the intact sperm cells to the bottom of the centrifuge tube. Following the centrifugation step, all or some of the supernatant is removed; which can be saved and later analyzed as the non-sperm fraction as it contains the DNA from any epithelial cells that may be present in the sample. The pellet fraction, possibly along with residual supernatant fraction, is resuspended in a resuspension buffer (e.g., Tris-HCl (50 mM, pH 8) and SDS (0.1%)). Reducing agent (e.g., 1-thiogylercol (1-TG), 11.5 mM) is added to the sample to break the disulfide bonds present on the sperm cells. Omission of the reducing agent, insufficient amounts of reducing agent, or excess amounts of reducing agent impair binding between the sperm cells and cellulose resin. The resuspended and reduced pellet fraction is mixed with a paramagnetic cellulose resin for 50 minutes. This step allows for binding between the sperm cells and the cellulose resin. The bound sperm cells are washed (e.g., four times) in a wash buffer (e.g., 50 mM Tris-HCl, pH 8; 0.1% SDS), and then the sperm-associated DNA is eluted from the resin via heating at 65° C. for 30 minutes with mixing in elution buffer (e.g., 50 mM Tris-HCl, 5.75 mM 1-TG, and 100 g/ml ProK). This final eluate contains the sperm-associated DNA and is compatible with quantification chemistries (e.g., POWERQUANT® (Promega Corp.) and STR genotyping chemistries (e.g., POWERPLEX®16HS (Promega Corp.), POWERPLEX®ESI/ESX (Promega Corp.), POWERPLEX®FUSION and POWERPLEX®FUSION 6C (Promega Corp.), IDENTIFILER® (ThermoFisher Scientific), GLOBALFILER™ 6-DYE™ (ThermoFisher Scientific), and INVESTIGATOR®24Plex (Qiagen)). Other embodiments of isolating/purifying sperm-associated DNA are contemplated and within the scope of the present disclosure.

The disclosure also provides a kit comprising two or more of: (a) a digestion agent (or concentration of a digestion agent) capable of efficiently lysing epithelial cells, but not sperm cells; (b) a reducing agent capable of breaking disulfide bonds present on sperm cells; (c) a cellulose resin; (d) a resuspension buffer; (e) a wash buffer; and (f) an elution buffer comprising a digestion agent and a reducing agent. Descriptions of the digestion agent, reducing agent, cellulose resin, wash buffer, elution buffer, and components thereof set forth above also apply to those same aspects of the aforementioned kit. The resuspension buffer may be any buffer suitable for putting pelleted cells and/or DNA back into suspension in a fluid. Suitable resuspension buffers are known in the art. An exemplary resuspension buffer comprises Tris-HCl (50 mM, pH 8) and SDS (0.1%) buffer.

The kit also desirably comprises instructions for use. Instructions included in the kit may be affixed to packaging material or may be included as a package insert. The instructions may be written or printed materials but are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

The kit may include a cartridge that comprises the cellulose resin, wash buffer, and one or more reagents useful for practicing the methods disclosed above. The cartridge may be disposable. The cartridge may include one or more containers holding the reagents, as one or more separate compositions, or, optionally, as admixture where the compatibility of the reagents will allow. The cartridge may also include other material(s) that may be desirable from a user standpoint, such as buffer(s), a diluent(s), and/or any other material useful in sample processing, washing, or conducting any other step of the method.

The various components of the kit optionally are provided in suitable containers as necessary.

The following example further illustrates the invention but, of course, should not be construed as in any way limiting its scope.

Examples

Figure 2:
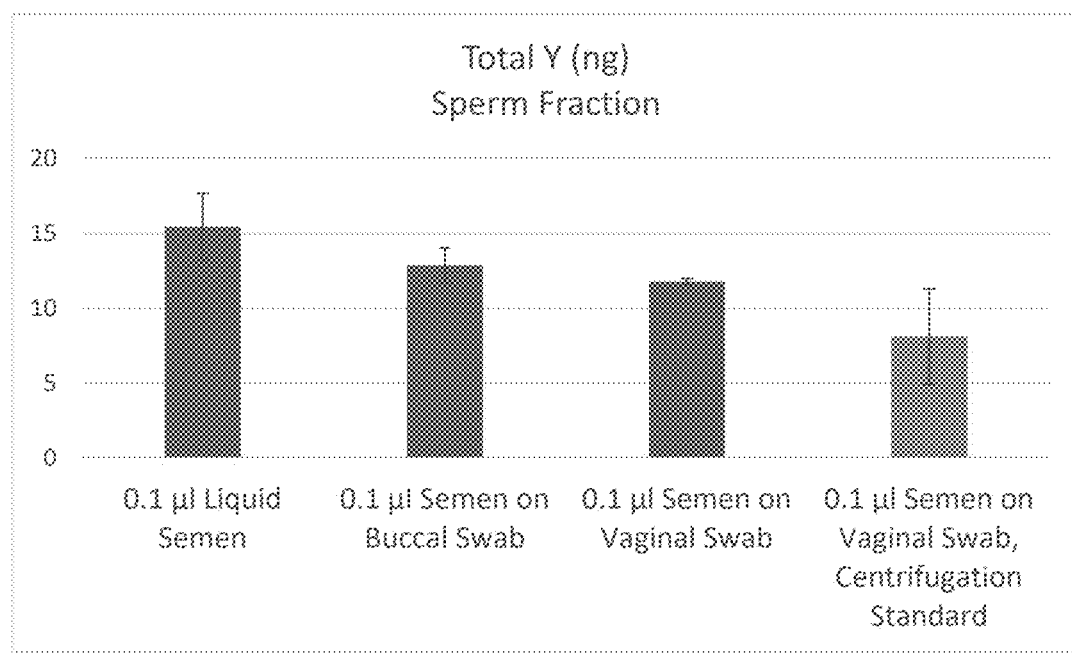
FIG. 2 is a graph showing overall yield of sperm-associated DNA isolated from various samples in accordance with the methods described herein. Data were obtained from a single experiment (n=3 for each condition) and quantified using the POWERQUANT® System (Promega Corp, Madison, WI). Bars represent the mean±the standard deviation.
Figure 3:
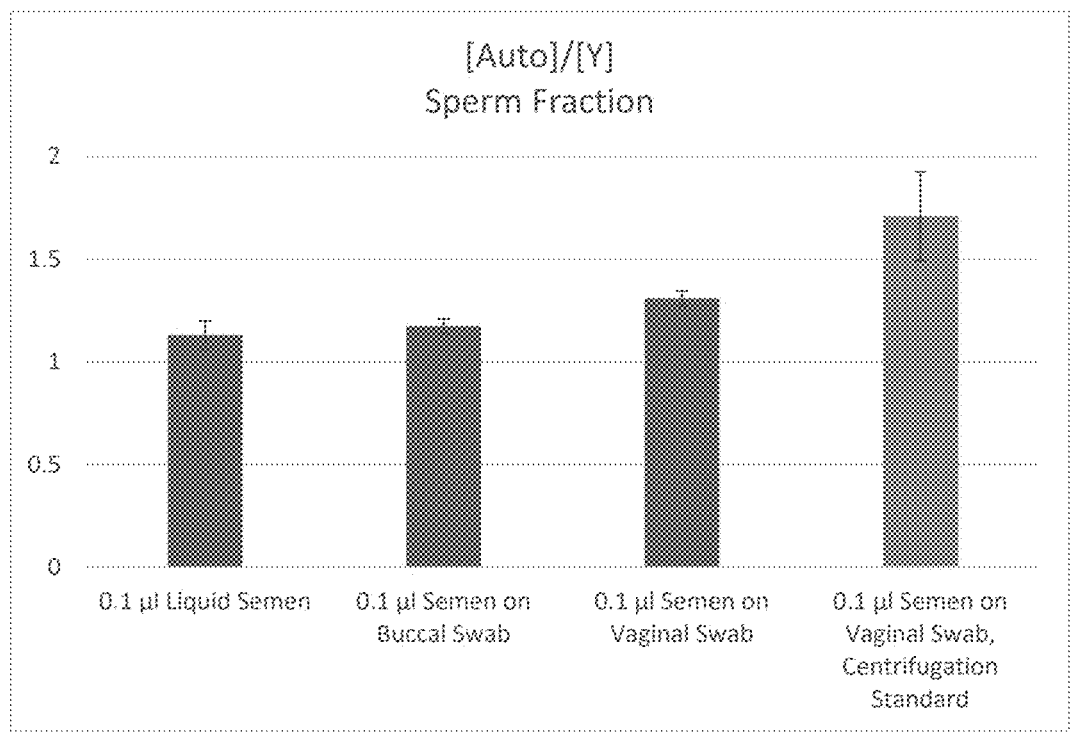
FIG. 3 is a graph showing the male DNA purity of the sperm-associated DNA isolated from various samples in accordance with the methods described herein. Starting material was calculated to have an [Auto]/[Y] ratio of approximately 120 for spotted buccal swab samples and approximately 1800 for spotted vaginal swab samples. An [Auto]/[Y] ratio close to one indicates that most of the female DNA was removed from the sample. Data were obtained from a single experiment (n=3 for each condition) and quantified using the POWERQUANT® System (Promega Corp, Madison, WI). Bars represent the mean±the standard deviation.

The methods described herein were performed using a variety of samples as inputs. Sperm-associated DNA was efficiently isolated from liquid semen, semen spotted onto buccal swabs from female donors, and semen spotted onto vaginal swabs, in terms of overall yield (FIG. 2) and male DNA purity (FIG. 3). The inventive method produces comparable results to the more labor-intensive centrifugation method.

Figure 4:
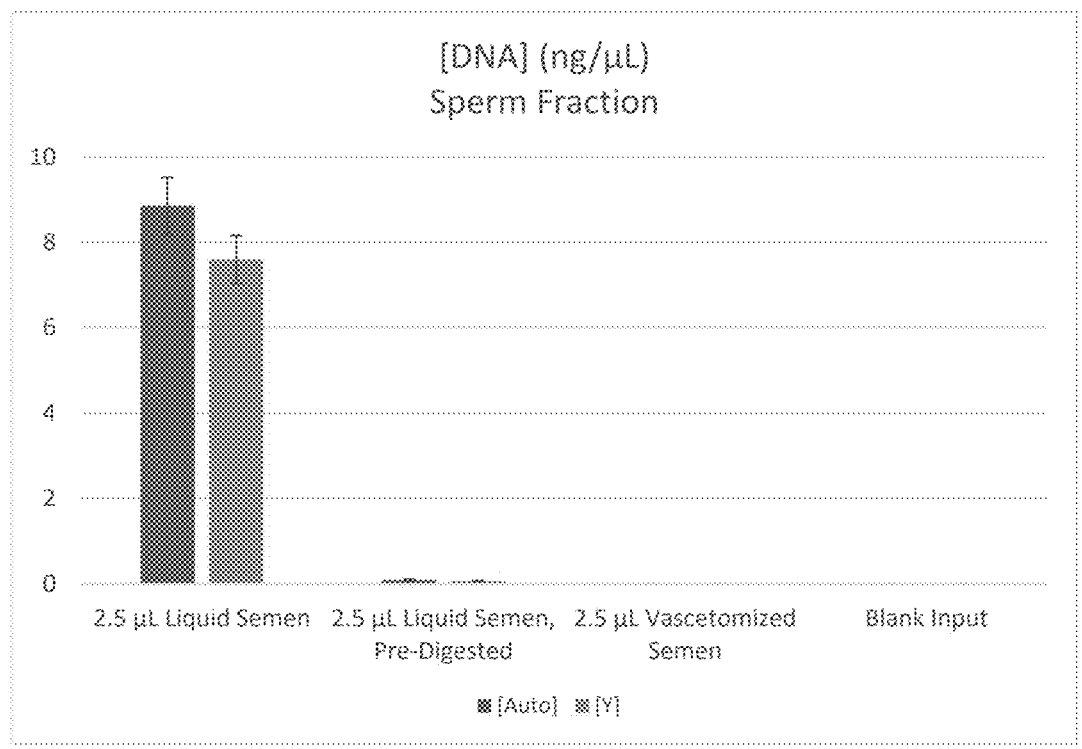
FIG. 4 is a graph showing that the methods described herein did not yield DNA from vasectomized semen samples or from blank inputs, and that sperm-associated DNA yields were greatly reduced when semen was pre-digested in the presence of reducing agent (5.75 mM 1-thioglycerol (1-TG)). Data were obtained from a single experiment (n=3 for each condition) and quantified using the POWERQUANT® System (Promega Corp, Madison, WI). Bars represent the mean±the standard deviation.
Figure 5:
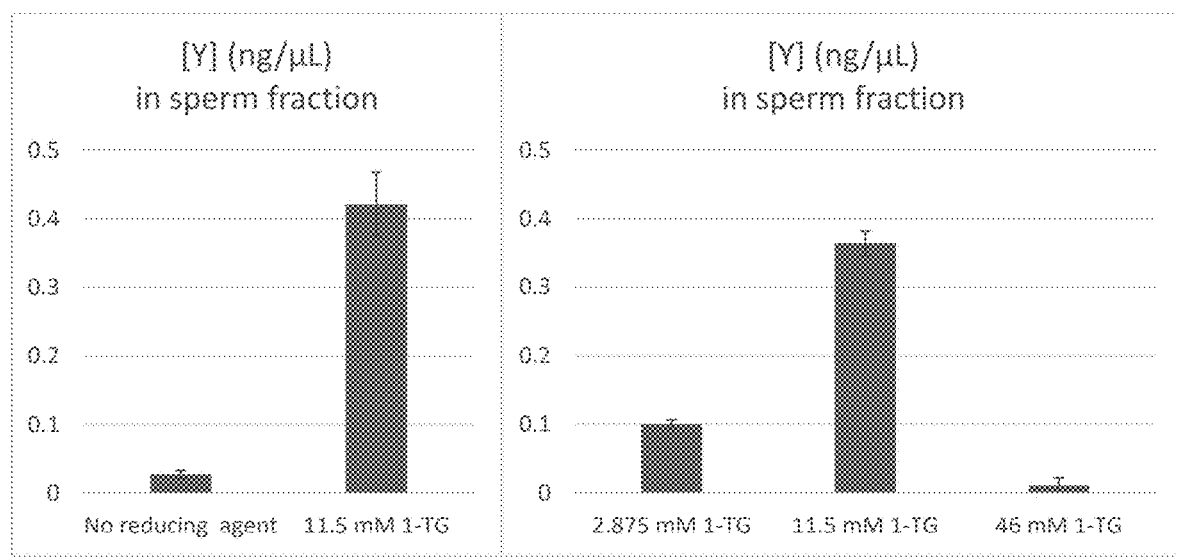
FIG. 5 displays two graphs illustrating the effects of reducing agent concentration on binding of sperm cells to a cellulose resin. Left: data were obtained from a single experiment (n=4 for each condition). Right: data were obtained from a single experiment (n=3 for each condition). The input material was 0.1 µL of liquid semen for each sample; the indicated concentration of 1-thioglycerol was added to the resuspension buffer and present during the binding reaction. Data were quantified using the POWERQUANT® System (Promega Corp, Madison, WI). Bars represent the mean±the standard deviation.

Appropriately, the inventive method did not yield DNA from vasectomized semen samples or from blank inputs (FIG. 4). Additionally, yields from this method were greatly reduced when the semen was pre-digested with reducing agent, as shown in FIG. 4. Finally, failure to include reducing agent (1-TG) in the binding reaction, or including a non-optimized concentration of reducing agent, greatly reduced the overall yield (FIG. 5).

Figure 6:
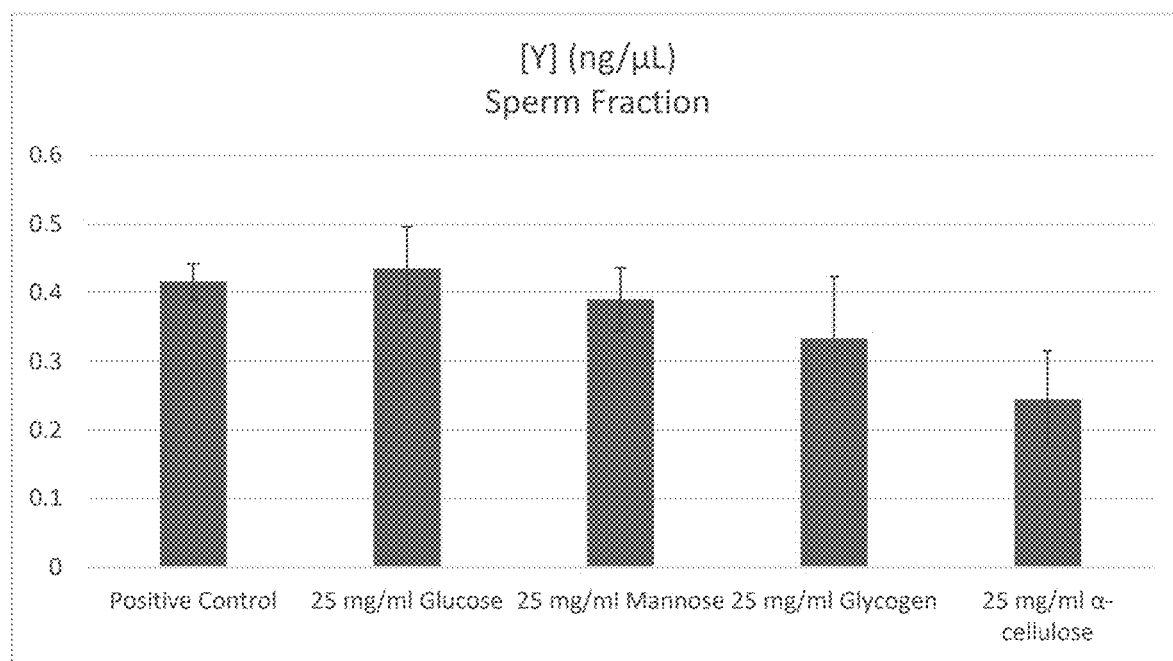
FIG. 6 is a graph illustrating the effects of various sugars on binding of sperm cells to a cellulose resin. Data were obtained from a single experiment (n=4 for each condition). The input material was 0.1 µL of liquid semen, and the indicated sugars were added to Well 1 of the MAXWELL® cartridges such that they were present during the binding reaction. Data were quantified using the POWERQUANT® System (Promega Corp, Madison, WI). Bars represent the mean±the standard deviation.

Several paramagnetic cellulose resins also were tested. Resins with an iron core surrounded by cellulose performed well in the assay, including Perloza MG 200 resin (Perloza s.r.o., Lovosice, Czech Republic) and the paramagnetic particle included in the MAXWELL® RSC ccfDNA Plasma Kit (Promega Corp., Madison, WI). Sperm cells likely were directly binding to the cellulose in the resin, as α-cellulose powder, when added to Well 1 of a Maxwell® cartridge, decreased overall yield, while neither glucose nor mannose had an observable effect (see FIG. 6).

The inventive method isolated sperm-associated DNA from postcoital samples (FIG. 7A-D). The resulting yields and purity were similar to the more labor-intensive centrifugation method.

Figure 9:
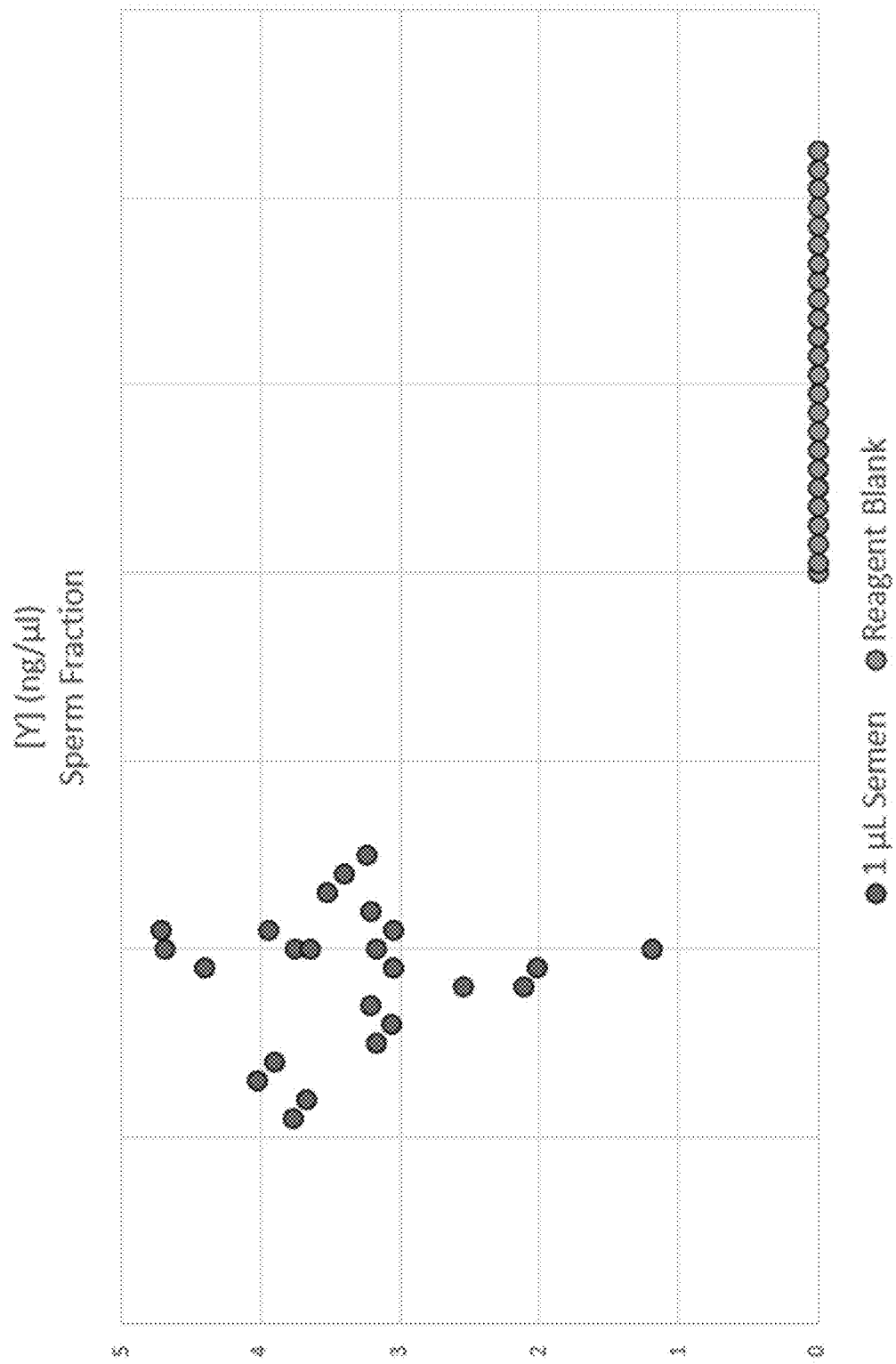
FIG. 9 is a set of graphs demonstrating that the methods described herein consistently and repeatedly purify sperm-associated DNA. For this experiment, twenty-four replicate samples, consisting of 1 μl semen each, and twenty-four reagent blanks were examined in parallel. This experiment utilized the alternate digestion protocol of 70° C. for 30 minutes. Data were obtained from a single experiment and quantified using the POWERQUANT® System (Promega Corp, Madison, WI); each dot represents an individual sample.

The inventive method extracted sperm-associated DNA from mock swab samples when the initial digestion parameters were adjusted to 30 minutes at 70° C. (instead of 10 minutes at 37° C.) (FIG. 8). Using these new parameters, the repeatability of the inventive method was tested by examining replicate samples and reagent blanks in parallel (FIG. 9). The method consistently purified sperm-associated DNA from each of the replicate samples.

Figures 10A, 10B:
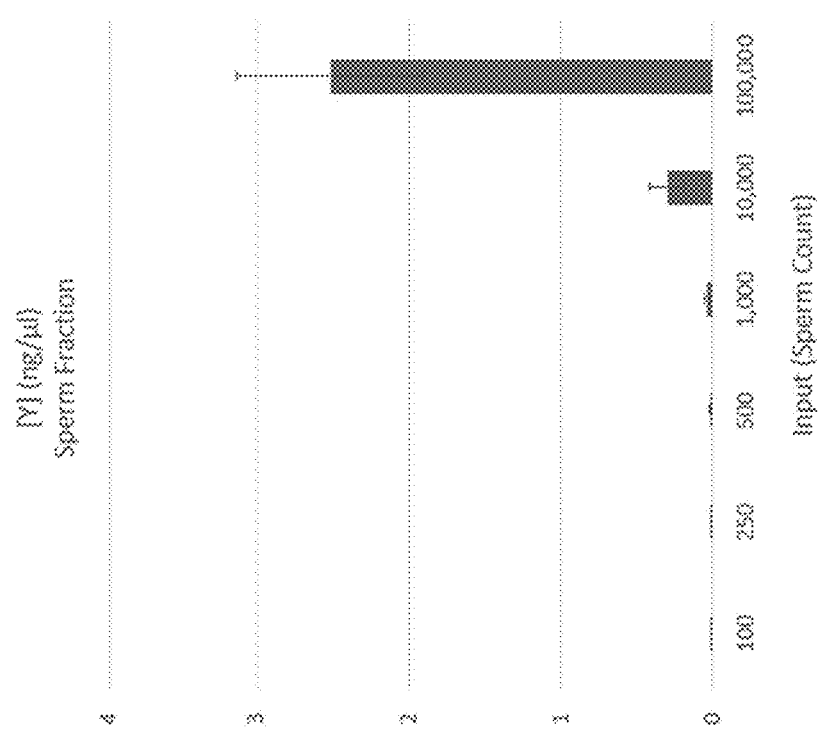
FIGS. 10A-B is a set of graphs demonstrating the sensitivity of the methods described herein. For this experiment, samples were created with a pre-determined number of sperm cells by diluting semen of a known sperm count.

Using the modified initial digestion conditions (i.e., 70° C. for 30 minutes), the sensitivity and specificity of the inventive method were examined. The sensitivity was tested using inputs with pre-determined sperm counts; samples were created by diluting semen of a known sperm count (BioIVT, Hicksville, NY). The inventive method yielded a detectable amount of sperm-associated DNA with inputs of as little as 250 sperm cells (FIG. 10A-B). The specificity was tested by mixing a fixed amount of semen with increasing amount of epithelial DNA derived from crude epithelial cell lysate. Even at the highest examined conditions (0.005 µl semen mixed with 5.5 mg of epithelial DNA), the method effectively isolated sperm-associated DNA (FIGS. 11A-C).

REFERENCES

The following references are herein incorporated herein in their entireties.

Gill et al., "Forensic application of DNA 'fingerprints,'" *Nature*, 318: 577-579 (1985);

Yoshida et al., "The modified method of two-step differential extraction of sperm and vaginal epithelial cell DNA from vaginal fluid mixed with semen," *Forensic Science International*, 72: 25-33 (1995);

Vandewoestyne M and Deforce D., "Laser capture microdissection in forensic research: a review," *Int J Legal Med*, 124: 513-521 (2010);

Garvin et al., "DNA Preparation from Sexual Assault Cases by Selective Degradation of Contaminating DNA from the Victim," *Journal of Forensic Sciences*, 54: 1298-1303 (2009);

Anslinger et al, "Application of sperm-specific antibodies for the separation of sperm from cell mixtures," *Forensic Science International: Genetics Supplement Series*, 1: 394-395 (2008);

Zhao et al., "Isolating Sperm from Cell Mixtures Using Magnetics Beads Coupled with an Anti-PH-20 Antibody for Forensic DNA Analysis," *PLOS ONE*, 11: e0159401 (2016); Albert L. Lehninger, *Principles of Biochemistry*, at 793-800 (Worth Pub. 1982);

Braasch and Corey, *Biochemistry*, 41(14): 4503-4510 (2002);

U.S. Pat. No. 5,034,506;

Butler, John M., *Advanced Topics in Forensic DNA Typing: Methodology*, Elsevier Inc.: MA, USA (2011);

Wahlestedt et al., *Proc. Natl. Acad. Sci. U.S.A.*, 97: 5633-5638 (2000); and

Wang, *J. Am. Chem. Soc.*, 122: 8595-8602 (2000).

The invention claimed is:

1. A method comprising:
 (a) contacting a sample comprising sperm cells with a digestion agent comprising a detergent and proteinase K to a concentration of 0.1 mg/ml to 1 mg/ml proteinase K under conditions capable of efficient lysis of epithelial cells but wherein a portion of the sperm cells remain unlysed;
 (b) removing the digestion agent from the sample, inactivating the digestion agent, or allowing the digestion agent to become inactivated;
 (c) adding a reducing agent to the sample, wherein the reducing agent breaks disulfide bonds present on the sperm cells, but wherein a portion of the sperm cells remain unlysed;
 (d) contacting the sample with a cellulose resin under conditions that the unlysed sperm cells bind to the cellulose resin;
 (e) washing the cellulose resin with a wash buffer; and
 (f) contacting the cellulose resin with an elution buffer capable of lysing the cellulose-resin-bound sperm cells and eluting sperm-associated DNA from the cellulose-resin-bound sperm cells.

2. The method of claim 1, wherein the detergent comprises sodium dodecyl sulfate (SDS).

3. The method of claim 1, wherein step (b) comprises providing sufficient time to allow the proteinase K to autoproteolyze and/or adding a chemical inhibitor to inactivate the proteinase K.

4. The method of claim 1, further comprising a step between steps (a) and (d) of separating a sperm-cell-enriched fraction of the sample from a sperm-cell-depleted fraction of the sample.

5. The method of claim 4, wherein the sperm-cell-enriched fraction is used in steps (d) through (f).

6. The method of claim 5, wherein the sperm-cell-depleted fraction is retained for subsequent analysis comprising obtaining sperm-depleted DNA from the sperm-cell-depleted fraction, and quantifying and/or genotyping the sperm-depleted DNA.

7. The method of claim 1, wherein the reducing agent comprises dithiothreitol (DTT), tris(2-carboxyethyl) phosphine (TCEP), 2-mercaptoethanol (BME), glutathione (GSH), and/or 1-thioglycerol (1-TG).

8. The method of claim 1, wherein the cellulose resin comprises a paramagnetic cellulose resin.

9. The method of claim 1, wherein the sperm-associated DNA is eluted from the cellulose resin in an elution buffer comprising a digestion agent and a reducing agent.

10. The method of claim 9, wherein the digestion agent comprises proteinase K and the reducing agent comprises DTT, TCEP, BME, GSH, and/or 1-TG.

11. The method of claim 9, wherein the sperm-associated DNA is eluted from the cellulose resin by heating the cellulose resin in the elution buffer.

12. A method of forensic analysis comprising performing the steps of claim 1 and comparing the sperm-associated DNA of the sample with a reference sample and/or a database.

13. The method of claim 12, further comprising determining whether a subject is the source of the sperm-associated DNA.

14. A method of forensic analysis comprising performing the steps of claim 6 and comparing the sperm-depleted DNA of the sample with a reference sample and/or a database and determining whether a subject is the source of the sperm-depleted DNA in the sample.

* * * * *